US008236946B2

(12) United States Patent
Bury

(10) Patent No.: US 8,236,946 B2
(45) Date of Patent: Aug. 7, 2012

(54) PROCESS FOR THE PREPARATION OF 17-0-VINYL-TRIFLATES AS INTERMEDIATES

(75) Inventor: Paul S Bury, Burnley (GB)

(73) Assignee: BTG International Limited, London (GB)

( * ) Notice: Subject to any disclaimer, the term of this patent is extended or adjusted under 35 U.S.C. 154(b) by 1161 days.

(21) Appl. No.: 11/660,792

(22) PCT Filed: Aug. 23, 2005

(86) PCT No.: PCT/GB2005/003283
§ 371 (c)(1),
(2), (4) Date: Mar. 30, 2007

(87) PCT Pub. No.: WO2006/021777
PCT Pub. Date: Mar. 2, 2006

(65) Prior Publication Data
US 2007/0282109 A1  Dec. 6, 2007

Related U.S. Application Data

(60) Provisional application No. 60/603,558, filed on Aug. 24, 2004.

(30) Foreign Application Priority Data

Aug. 24, 2004 (GB) .................................. 0418900.7
Aug. 24, 2004 (GB) .................................. 0418901.5

(51) Int. Cl.
*C07J 43/00* (2006.01)
(52) U.S. Cl. ........................................................ 540/95
(58) Field of Classification Search .................. 540/120, 540/95
See application file for complete search history.

(56) References Cited

U.S. PATENT DOCUMENTS
5,338,875 A    8/1994  DeCamp et al.

FOREIGN PATENT DOCUMENTS
| EP | 1 553 082 A1 | 7/2005 |
| WO | WO 93/20097 A | 10/1993 |
| WO | WO 95/09178 | 4/1995 |
| WO | WO 2004/000795 A | 12/2003 |

OTHER PUBLICATIONS

Potter, G.A., et al; "Novel steroidal inhibitors of human cytochrome P450-17alpha (17-alpha-hydroxylase-C-17,20-lyase): Potential agents for the treatment of prostatic cancer"; *Journal of Medicinal chemistry, American Chemical Society*, Washington, US, vol. 38, No. 13, 1995, pp. 2463-2471, XP002302489.
Haidar, Samer, et al; "Novel steroidal pyrimidyl inhibitors of P450 17 (17alpha-hydroxylase/C17-20-lyase)" *Archiv Der Pharmazie* (Weinheim), vol. 334, No. 12, Dec. 2001; pp. 373-374, XP002355060.
Orsini, F., et al; "Influence of the catalyst of the PDO-mediated reactions of BrZnCH(CH3)COOtBu with vinyl and aryl triflates"; *Journal of Organometallic Chemistry*; vol. 367, 1989; pp. 375-382; XP002355061.
Stang, P.J., et al; "Perfluoroalkanesulfonic Esters: Methods of Preparatino and Applications in Organic Chemistry"; *Synthesis*, Georg Thieme Verlag, Stuttgart, DE; 1982, pp. 85-126; XP000919260.
Cacchi, S., et al; "Palladium Catalysed Reduction of Enol Triflates to Alkenes"; *Tetrahedron Letters*; vol. 25, No. 42; 1984; pp. 4821-4824; XP002355062.
Hassdenteufel, J.R., et al; "Vinyl Cations 33: 1-Alkene-3-Yne-2-YL Triflates, Precursors of Triple Bond Stabilized Vinyl Cations—Synthesis and first Solvolytic Studies"; *Tetrahedron Letters*; vol. 21, 1980, pp. 503-506; XP002355063.
Stang, P.J., et al; "Synthesis of 1-(Ethylnyl)-vinyl Trifluoromethanesulfonates"; *Synthesis*; 1979; pp. 438-440; XP002355064.
Agnes, Anne, et al; "Formal hydride transfer from NADH analogues: 1-Benzyl-4-tert-butyl-1,4-dihydronicotinam idle as a mechanistic probe"; *Journal of the American Chemical Society*; vol. 115, No. 22; 1993; pp. 10224-10230; XP002355065.
Deutsch, E., et al; "Noncoordinating Buffers. I. Synthesis and Characterization of Water-Soluble Derivatives of 2,6-Di-tert-butylpyridine"; *Journal of Organic Chemistry*; vol. 38, No. 6, 1973; pp. 1123-1126; XP002355066.
Hopkins, H., et al; "Thermodynamics of Ionization of Some Mono- and Disubstituted tert-Butylpyridinium Ions in Alcohol-Water Systems"; *Journal of the American Chemical Society*; vol. 99, No. 7; 1977; pp. 2069-2072; XP002355067.
Hopkins, H., et al; "Basicities of the 2-, 4-, 2,4-Di- and 2,6-Disbustituted tert-Butyl Pyridines in the Gas Phase and Aqueous Phase: Steric Effects in the Solvation of tert-Butyl-Substituted Pyridines and Pyridinium Cations"; *Journal of the American Chemical Society*; vol. 106, No. 16; 1984; pp. 4341-4348; XP002355068.
Arnett, E.A., et al; "Hydrogen Bonding Spectra of Pyridinium Hydrocholorides in Dimethyl Sulfoxide Solution and as Mulls"; *Journal of the American Chemical Society*; vol. 100, No. 1; 1978; pp. 214-216; XP002355069.
Brown, H.C., et al; "Preparation and Reactions of 2,6-Di-t-butylpyridine and Related Hindered Bases. A Case of Steric Hindrance toward the Proton"; *Journal of the American Chemical Society*; vol. 88, No. 5; 1966; pp. 986-992; XP002355070.
Katritzky, A.R., et al; "One-Carbon Homologation of Carboxylic Acids via BtCH$_2$TMS: A Safe Alternative to the Arndt-Eistert Reaction"; *J. Org. Chem.*; vol. 66(16); pp. 5606-5612 (2001).
Ling, Y., et al; "17-Imidazolyl, Pyrazolyl, and Isoxazolyl Androstene Derivatives. Novel Steroidal Inhibitors of Human Cytochrome C$_{17,20}$-Lyase (P450$_{17}$α)"; *J. Med. Chem.*; vol. 40(20); pp. 3297-3304 (1997).

(Continued)

*Primary Examiner* — Patricia Morris
(74) *Attorney, Agent, or Firm* — Nixon & Vanderhye

(57) ABSTRACT

Process for the preparation of a compound of formula (I) as defined herein by (i) triflating a ketone of formula (II) as defined herein to form a triflate of formula (III) as defined herein and (ii) reacting the compound of the formula (III) to form a compound of the formula (I) or a pharmaceutically-acceptable salt thereof. The triflating step is conducted in the presence of a base comprising a tertiary or heterocyclic amine such that the p$K_a$ of the conjugate acid at 25° C. is within the range 5.21 to 12. The base is selected from pyridine, 2,6-lutidine, N-methylmorpholine, 1,4-diazabicyclo[2.2.2]octane (DABCO), trimethylamine, triethylamine, N,N-diisopropylethylamine (DIPEA), quinuclidine and 1,8-diazabicyclo[5.4.0]undec-7-ene (DBU).

15 Claims, No Drawings

OTHER PUBLICATIONS

Hartmann, R.W., et al, "Synthesis and Evaluation of Novel Steroidal Oxime Inhibitors of P450 17 (17α-Hydroxylase/C17-20-Lyase) and 5α-Reductase Types 1 and 2"; *J. Med. Chem.*; vol. 43(22); pp. 4266-4277 (2000).

Schweder, B., et al; "$\Delta^{16}$-20-Ketosteroide durch $C_2$-Verlangerung aus $\Delta^{16}$-17-substituierten Steroiden"; *J. Prakt. Chem.*; vol. 335(5); pp. 439-444 (1993).

Ciattini, P.G., et al; "A New Synthesis of the Corticosteroid Side Chain"; *Tetrahedron Letters*; vol. 31(13); pp. 1889-1892 (1990).

Ciattini, P.G., et al; "Palladium-Catalyzed β-Vinylation of Vinyl Acetate with Enol Triflates. An Entry to 1-Acetoxy-1,3-Dienes"; *Tetrahedron Letters*; vol. 32(12); pp. 1579-1582 (1991).

Haidar, S., et al; "Effects of novel 17α-hydroxylase/C17, 20-lyase (P450 17, CYP 17) inhibitors on androgen biosynthesis in vitro and in vivo"; *Journal of Steroid Biochemistry & Molecular Biology*; vol. 84; pp. 555-262 (2003).

Cacchi, S., et al; "Palladium-Catalyzed Reaction of Enol Triflates with 1-Alkynes. A New Route to Conjugated Enynes"; *Synthesis*; pp. 320-332 (1986).

Orsini, F., et al; "Pd (0)-Mediated Cross-Coupling of Reformatsky Reagents with Vinyl- and Aryl Triflates"; *Synthetic Communications*; vol. 17(12); pp. 1389-1402 (1987).

PCT International Preliminary Report on Patentability; Int'l Application No. PCT/GB2005/003283, Int'l Filing Date Aug. 23, 2005 (11 pgs).

Co-pending U.S. Appl. No. 11/660,869, filed Feb. 22, 2007.

PROCESS FOR THE PREPARATION OF 17-0-VINYL-TRIFLATES AS INTERMEDIATES

This application is the U.S. National Phase of International Application PCT/GB2005/003283, filed 23 Aug. 2005, which designated the U.S. PCT/GB2005/003283 claims priority to British Application No. 0418900.7 filed 24 Aug. 2004, and British Application No. 0418901.5 filed 24 Aug. 2004, and Provisional Application No. 60/603,558, filed 24 Aug. 2004. The entire content of these applications are incorporated herein by reference.

This invention relates to a process for the preparation of the compound abiraterone, or a salt or derivative thereof.

Abiraterone acetate of formula:

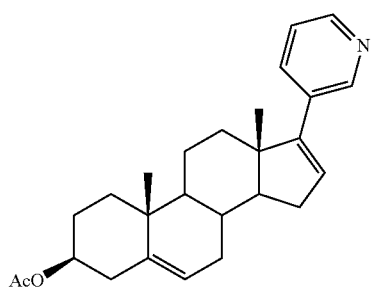

is a potent selective, orally active inhibitor of the key enzyme in testosterone synthesis, 17α-hydroxylase-C17,20-lyase, also known as steroid 17α-monooxygenase inhibitor or Human Cytochrome $P450_{17\alpha}$. Suppression of testosterone synthesis has been demonstrated with abiraterone acetate in patients with prostate cancer.

The compound was first disclosed in WO-A-93/20097, with a further synthetic method to the compound in WO-A-95/09178 (both British Technology Group Limited). In particular, WO-A-95/09178 discloses the synthesis of a compound of formula:

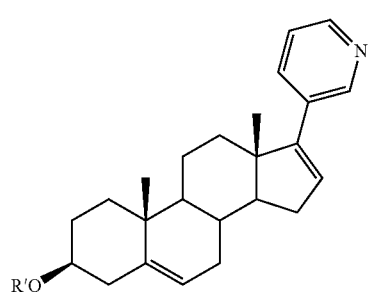

where the 3β substituent R' is hydrogen or a lower acyl group having 2 to 4 carbon atoms. One of the methods disclosed makes this from the corresponding ketone via the steroidal enol triflate(trifluoromethylsulfonate):

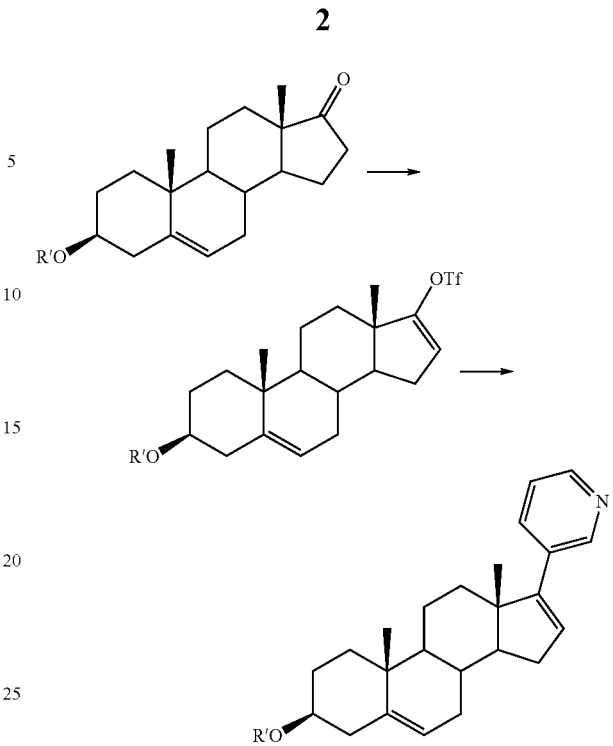

WO-A-95/09178 suggests replacing the triflate with a corresponding vinyl iodide intermediate, and uses this to make compounds by reacting this with a (3-pyridyl)-substituted borane of formula:

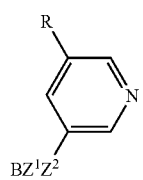

wherein R represents a hydrogen atom or an alkyl group of 1-4 carbon atoms and $Z^2$ and $Z^2$ independently represent hydroxy or alkoxy or alkyl of 1-3 carbon atoms each or $Z^1$ and $Z^2$ together represent an alkylenedioxy group of 2 or 3 carbon atoms.

The triflate intermediate is also reported in *J. Med. Chem.* (1995), 38(13), 2463-71 (Potter et al.); *J. Med. Chem.* (1997), 40(20), 3297-3304 (Ling et al.); *J. Med. Chem.* (2000), 43(22), 4266-4277 (Hartmann et al.); *Journal für Praktische Chemie/Chemiker-Zeitung* (1993), 335(5), 439-44 (Schweder et al.); *Tet. Lett.* (1990), 31(13), 1889-1892 and *Tet. Lett.* (1991), 32(12), 1579-82 (both Ciattini et al.); *Archiv der Pharmazie* (Weinheim, Germany) (2001), 334(12), 373-374 and *Steroid Biochem. Molec. Biol.* (2003), 84, 555-562 (both Haidar et al.); *Synthesis* (1986), 320-322 (Cacchi et al.); and *J. Organomet. Chem.* (1989), 367(3), 375-82 and *Synth. Commun.* (1987), 17(12), 1389402 (both Orsini et al.). All of these references prepare the triflate intermediate according to the method recommended in a review entitled "Perfluoroalkanesulfonic Esters: Methods of Preparation and Application in Organic Chemistry", *Synthesis,* 1982, 85-126 (Stang et al.).

Page 107 of the review advocates against the use of simple bases such as pyridine, lutidine or triethylamine, as these give undesirable by-products at the triflate stage. Stang et al. recommend the use of 2,6-di-tert-butyl-4-methylpyridine (DT- BMP) instead, in spite of that fact that this base is expensive. Thus all the reported syntheses of the triflate intermediate for abiraterone up to now have used DTBMP, or occasionally 2,6-di-tert-butylpyridine.

The present inventors have observed that the original triflate reaction, which up to now appeared not to be the preferred route, still had certain attractive features. However, they also observed that using the base DTBMP when R' is a lower acyl group can lead to elimination of the acid, giving an undesirable by-product of formula:

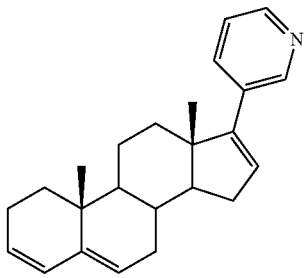

We have now developed an improved route in which the production of the undesirable by-product is kept down to acceptable levels. This means that the purification process is simplified, as expensive and time-consuming column chromatography steps can be eliminated. As this does not use the expensive reagent DTBMP, contrary to the teaching of Stang et al., the route is made commercially more attractive still.

Accordingly the present invention comprises a process for the preparation of a compound of formula (I):

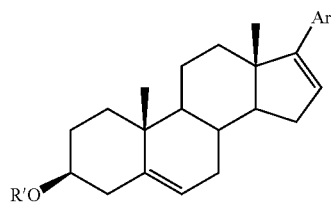

(I)

where Ar represents an optionally substituted five- or six membered fully unsaturated ring containing at least one nitrogen atom and joined to the main ring system by means of a carbon-carbon bond; and R' represents hydrogen or a lower acyl group having 2 to 4 carbon atoms;

or a pharmaceutically-acceptable salt thereof;

including a triflating step by which a ketone of formula (II) is converted into a triflate of formula (III):

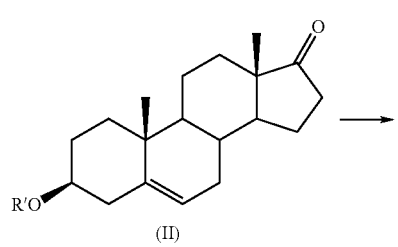

(II)

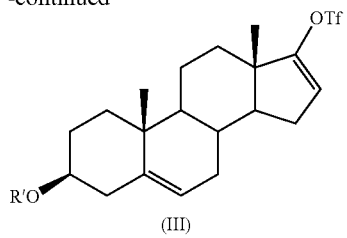

(III)

wherein R' is as defined above, or a protected derivative thereof;

the triflating step being conducted in the presence of a base comprising a tertiary or heterocyclic amine such that the $pK_a$ of the conjugate acid at 25° C. is within the range 5.21 to 12.

Using the present invention, a method for the preparation of the compound of formula (I) is possible which requires no chromatographic purification at any stage of the synthesis.

The $pK_a$ of the conjugate acid is the negative logarithm of the acid dissociation constant, $K_a$, and generally refers to ability of an ionizable group of the organic compound to donate a proton ($H^+$) in aqueous media. However, in the event that the compound is not soluble in water, the value used may refer to the dissociation constant in an aqueous mixture containing a co-solvent such as ethanol.

Preferred bases include those set out in Table 1:

TABLE 1

| Preferred bases | |
|---|---|
| Base | $pK_a$ of conjugate acid at 25° C. |
| pyridine | 5.21 |
| 2,6-lutidine | 6.75 |
| N-methylmorpholine | 7.38 |
| 1,4-diazabicyclo[2.2.2]octane (DABCO) | 8.82 |
| trimethylamine | 9.81 |
| triethylamine | 10.6 |
| N,N-diisopropylethylamine (DIPEA) | 11 |
| quinuclidine | 11.0 |
| 1,8-diazabicyclo[5.4.0]undec-7-ene (DBU) | 12 |

Preferably the $pK_a$ of the conjugate acid at 25° C. is within the range 6.75 to 10.6. Most preferably the base is 2,6-lutidine or triethylamine.

By way of comparison, the $pK_a$ of the conjugate acid of 2,6-di-tert-butyl-4-methylpyridine is 4.41 in 50% EtOH solvent at 27±2° C.—see *J. Org. Chem.* (1973), 38, 1123-1126 (Deutsch et al.). The $pK_a$ of the conjugate acid of 2,6-di-tert-butylpyridine is 4.95. Both fall outside the range specified in the present invention.

Preferably the triflating step is carried out in a solvent comprising a chlorineated organic solvent or an organic ester. Suitable organic esters include ethyl acetate. Preferably the solvent is a chlorinated organic solvent such as chloroform, and in particular dichloromethane or 1,2-dichloroethane.

Ar may represent any optionally substituted five- or six membered fully unsaturated ring containing at least one nitrogen atom and joined to the main ring system by means of a carbon-carbon bond. The optionally substitution may take the form of an alkyl group of 1-4 carbon atoms. Preferably the fully unsaturated ring contains one or two heteroatoms, with at least one of them being nitrogen. Five-membered fully unsaturated rings include pyrrole, imidazole, pyrazole, isothiazole and isoxazole. Six-membered aromatic rings fully unsaturated include the aromatic rings pyridine, pyrazine, pyrimidine and pyridazine. Preferably Ar represents an unsubstituted five-membered fully unsaturated ring, or a six-membered aromatic ring optionally substituted with a single substituent.

In the case of Ar representing an unsubstituted five-membered fully unsaturated ring, preferred values include:

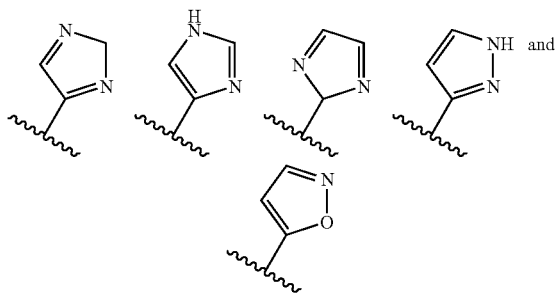

In the case of Ar representing a six-membered aromatic ring optionally substituted with a single substituent, preferred values include:

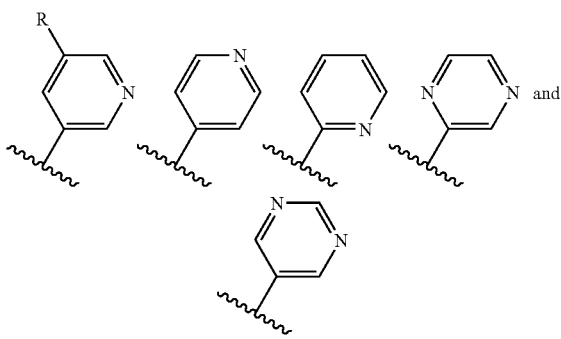

where R represents a hydrogen atom or an alkyl group of 1-4 carbon atoms.

In the case where R' represents hydrogen, the protecting group could be any suitable group for protecting alcohols, as discussed in "Protective groups in organic synthesis" 3$^{rd}$ Ed, Theodora W Greene and Peter G Wuts, published by John Wiley, ISBN 0-471-16019-9. For example, it might be protected as a benzyl, methoxymethyl (MOM) or silyl ether.

Preferably R' represents a lower acyloxy group, in which case no further protection would normally be necessary, especially acetyl.

Preferably the compound of formula I is a compound of formula:

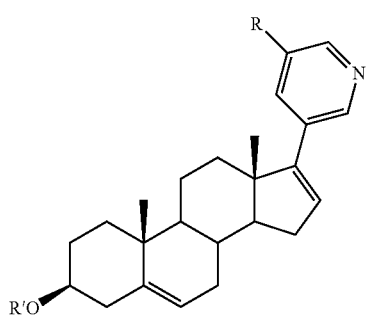

in which R and R' are as defined as above, with R preferably representing a hydrogen atom. Most preferably R' represents acetyl and R represents a hydrogen atom, the compound of formula (I) being abiraterone acetate.

The preferred triflating agent is triflic anhydride (Tf$_2$O). To minimize decomposition of the product, preferably the base is added to the reaction mixture shortly after the triflic anhydride, say fifteen minutes or less. The reaction mixture is preferably quenched within an hour after the addition of the base, again to minimize decomposition of the product.

We have observed that the use of large excesses of base lead to poor conversion of the ketone of formula (II) into the triflate of formula (III), and that use of large excesses of triflic anhydride can lead to rapid decomposition of the product. For optimum conversion of the ketone of formula (II) into the triflate, the number of equivalents of triflic anhydride is preferably not lower than the number of equivalents of base. We have also observed that reducing the amount of base to sub-stoichiometric levels did not affect the conversion.

Thus preferably the triflating step is performed using between 1.0 and 1.5 equivalents, more preferably between 1.1 and 1.4 equivalents, of triflic anhydride relative to the ketone of formula (II); and between 0.75 and 1.5 equivalents of base, more preferably between 0.8 and 1.4 equivalents, relative to the ketone of formula (II), wherein the number of equivalents of triflic anhydride is greater than or equal to the number of equivalents of base. More preferably, the number of equivalents of triflic anhydride is greater than the number of equivalents of base.

The preparation of the ketone of formula (II), and the conversion of the triflate of formula (III) to a compound of formula (I), are by known methods. Thus, the triflate of formula (III), or a protected derivative thereof, may be reacted with a substituted borane of formula BZ$^1$Z$^2$Ar, wherein Ar is as defined above and Z$^1$ and Z$^2$ independently represent hydroxy or alkoxy or alkyl of 1-3 carbon atoms each or Z$^1$ and Z$^2$ together represent an alkylenedioxy group of 2 or 3 carbon atoms; in the presence of a palladium complex and a polar solvent, using the Suzuki coupling. This is disclosed in WO-A-93/20097, using a (3-pyridyl)-substituted borane of formula:

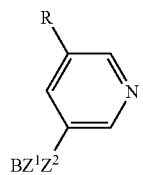

in which R represents a hydrogen atom or an alkyl group of 1-4 carbon atoms.

The conversion of the triflate of formula (III) to the following compound types:

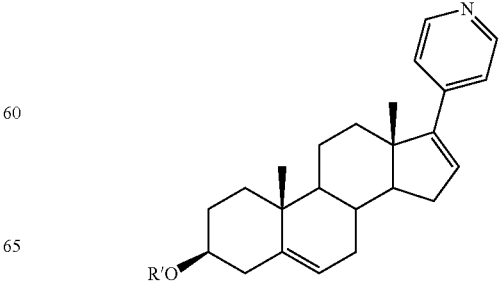

-continued

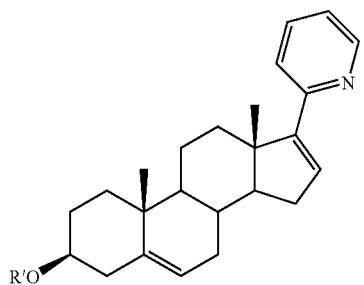

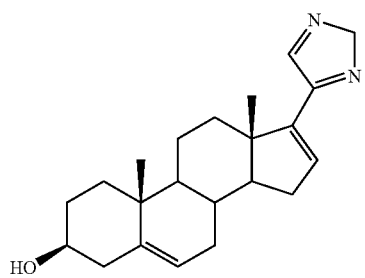

is disclosed in *J. Med. Chem.* (1995), 38(13), 2463-71 (Potter et al.). The conversion to the following compounds:

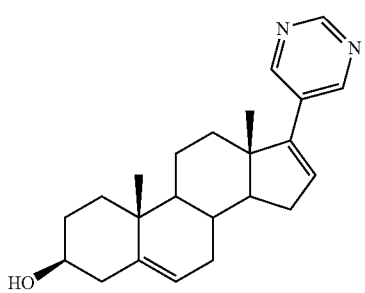

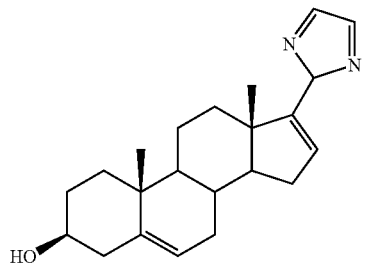

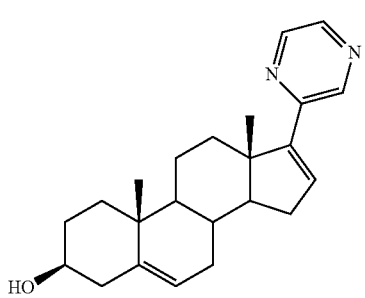

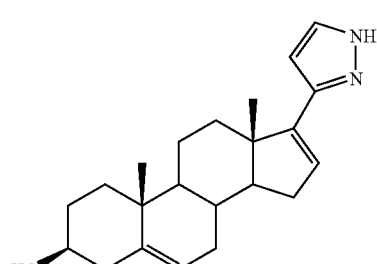

is disclosed in *Archiv der Pharmazie* (2001), 334(12), 373-374 and *J. Steroid Biochem. Molec. Biol.* (2003), 84, 555-562 (both Haidar et al.) and in *J. Med. Chem.* (2005), 48(8), 2972-2984 (Venkatesh et al.). The conversion to the following:

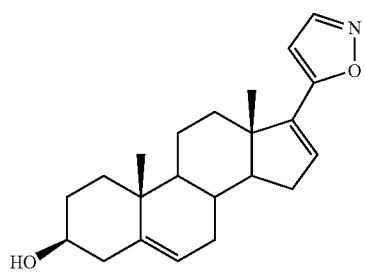

is disclosed in U.S. Pat. No. 5,994,334 and WO-A-98/33506 (University of Maryland at Baltimore). All these methods may be used in the present invention.

The compounds of formula (I) may be reacted further to form other derivatives. Thus they may be reduced as disclosed in *J. Med. Chem.* (1995), 38(13), 2463-71 (Potter et al.), where compounds of the following type are prepared:

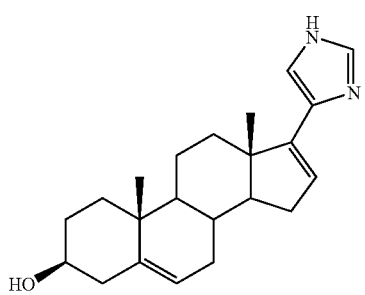

is disclosed in *J. Med. Chem.* (1997), 40(20), 3297-3304 (Ling et al.). The synthesis of the following compounds:

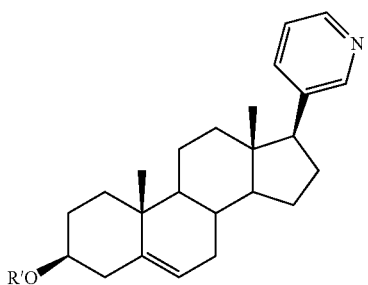

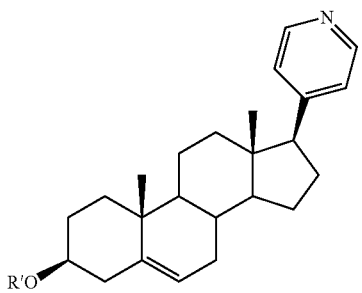

using hydrazine and acetic in ethanol, and sodium bis(2-methoxyethoxy)-aluminium hydride (Red-Al) and zinc chloride in THF, respectively.

Alternatively they may be oxidized as disclosed in *Archiv der Pharmazie* (2001), 334(12), 373-374 (Haidar et al.), where the following compound is prepared:

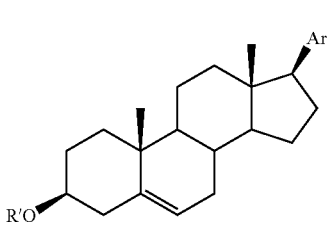

Thus in a further aspect of the invention the compound of formula (I), or a protected derivative thereof, is further reacted using a reducing agent to give a compound of formula (IV) or (IVA):

(IV)

or using an oxidizing agent to give a compound of formula (V):

(IVA)

(V)

wherein R' and Ar are is as defined above.

The compounds of formula (I) may be prepared as salts, e.g. the hydrochloride and converted to the free base form and thereafter to such other conventional pharmaceutically acceptable acid addition salts as acetates, citrates, lactates, alkanesulfonates (e.g. methanesulfonate), and optionally substituted tartrates as may seem appropriate.

In this specification the term "alkyl" includes both straight and branched chain. An analogous convention applies to other generic terms such as "alkoxy", "acyl" and "alkylenedioxy".

It is to be understood that all the ketones of formula (II) disclosed may exhibit the phenomenon of tautomerism and that the formulae shown in this specification represent only one of the possible tautomeric forms. It is to be understood therefore that the invention is not limited merely to any one tautomeric form which is illustrated. For example, the ketone of formula (II) may also exist as an enol of formula (IIA)

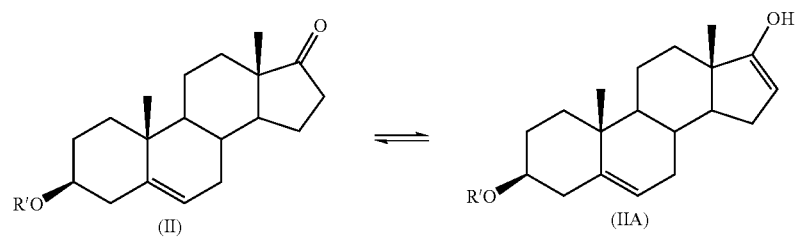

The invention is illustrated by the following Examples.

EXAMPLE 1

Preliminary Investigations into Reaction Steps

Step 1—Formation of the Triflate

The formation of the triflate may also give the eliminated impurity 4, which is very difficult to remove by crystallisation:

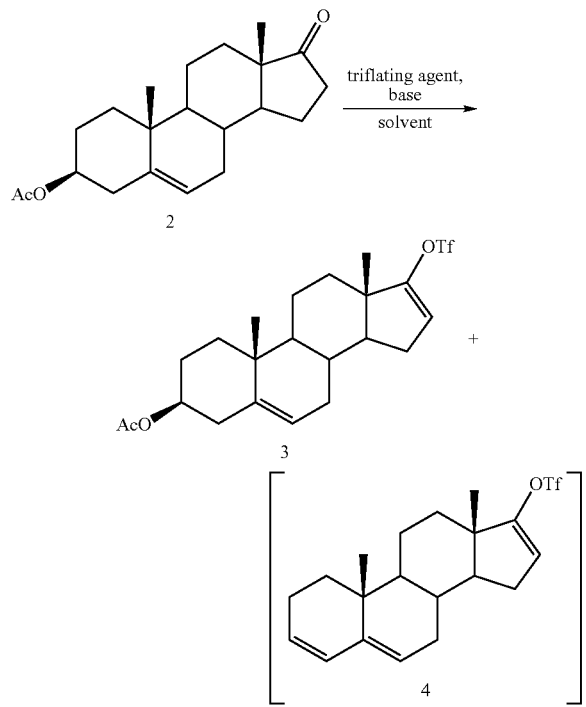

A series of bases was tested using dichloromethane as the solvent (Table 2). The % conversion and levels of the impurity 4 were measured by $^1$H NMR.

TABLE 2

Alternative bases for the formation of the triflate

| Triflating agent | Base | Solvent | Time | % conversion[2] | % 4[2] |
|---|---|---|---|---|---|
| Tf$_2$O (1.0 eq) | 2,6-lutidine (1.2 eq) | DCM | 24 hrs | 60% | 0% |
| Tf$_2$O (1.1 eq) | 2,6-lutidine (1.4 eq) | DCM | 3 hrs | 25% | 0% |
| Tf$_2$O (1.1 eq) | 2,6-lutidine (1.7 eq) | DCM | 2.5 hrs | 13% | 0% |
| Tf$_2$O (1.1 eq.) | 2,6-lutidine (1.0 eq.) | DCM | 4.5 hrs[1] | 85% | 0% |
| Tf$_2$O (1.1 eq) | Et$_3$N (1.4 eq) | DCM | 3 hrs | 40% | 0% |
| Tf$_2$O (1.1 eq) | Et$_3$N (1.7 eq.) | DCM | 2.5 hrs | 7% | 0% |
| Tf$_2$O (1.1 eq) | Et$_3$N (1.0 eq) | DCM | 1.5 hrs | 50% | 0% |
| Tf$_2$O (1.1 eq.) | Et$_3$N (1.0 eq.) | DCM | 4.5 hrs[1] | 77% | 0% |
| Tf$_2$O (1.1 eq.) | $^i$Pr$_2$EtN (1.0 eq.) | DCM | 4.5 hrs[1] | 80% | 0% |
| Comparative examples: | | | | | |
| Tf$_2$O (1.0 eq) | 2,6-di-tert-butyl-4-methyl pyridine (1.2 eq) | DCM | 16 hrs | 80% | Trace |
| Tf$_2$O (1.1 eq) | 2,6-di-tert-butyl-4-methyl pyridine (1.4 eq) | DCM | 3 hrs | 100% | 17% |

[1]Base added to a mixture of 2 and triflic anhydride.
[2]Conversion and % 4 determined by $^1$H NMR.

Repeating the reaction conditions reported in the prior art, using 2,6-di-tert-butyl-4-methyl pyridine as the base, went to completion when 1.4 equivalents of base were used. However, 17% of the product was the eliminated impurity.

When the conditions were repeated using 2,6-lutidine and Et$_3$N as the base (1.4 eq.) the reactions proceeded to around 40% conversion with no evidence of the eliminated product 4.

It had been demonstrated that the reaction proceeded further with a higher equivalency of 2,6-di-tert-butyl-4-methyl pyridine However, when 2,6-lutidine or Et$_3$N was used as the base, the reaction was inhibited. Therefore the amount of base was cut to 1 eq. and the conversion increased to 50% after 90 minutes.

This indicated that the reaction was inhibited by excess base, so the procedure was changed to a slow addition of the base (0.76 mmol. in 15 minutes) to a mixture of 2 and Tf$_2$O. The reaction reached around 80% conversion in 4.5 hours with Et$_3$N, 2,6-lutidine and $^i$Pr$_2$EtN.

When the addition time was extended to 3.5 hours the conversion remained around 80% with all the bases. However when the addition time was reduced to 2 minutes the reaction proceeded to only 45% conversion.

Step 2—The Suzuki Coupling

The Suzuki coupling was performed using reported methods. The product of the triflate formation was used in the Suzuki coupling unpurified.

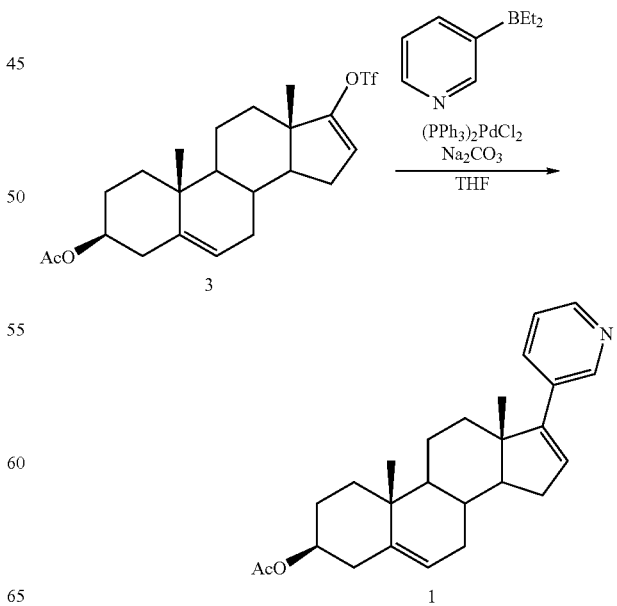

EXAMPLE 2

Larger Scale Synthesis of Abiraterone Acetate 1

Synthesis was conducted as in Scheme 1.

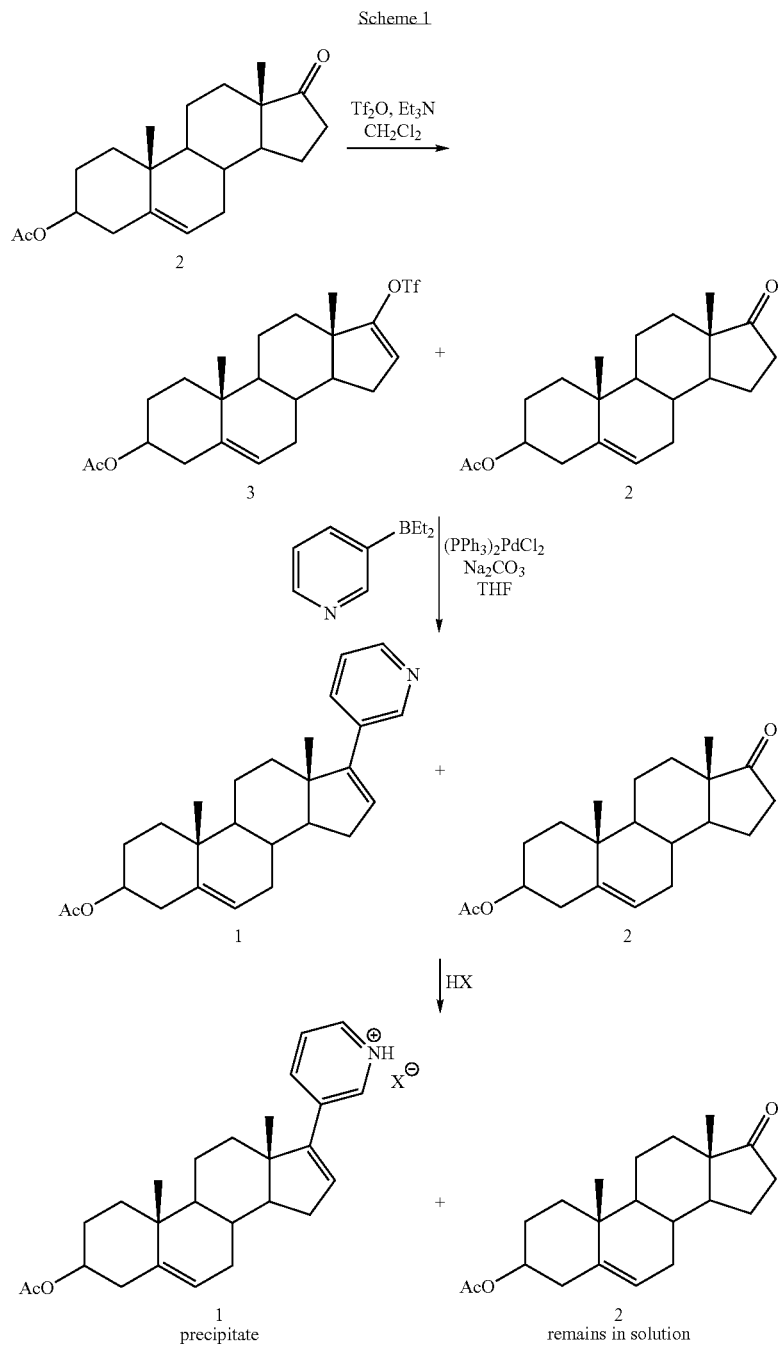

The optimised route was performed on a 10 g scale. The formation of the triflate yielded the crude product in an 80% yield (11.20 g) with a product to starting material ratio of 3:1.

The Suzuki reaction was performed on the crude product using a catalyst loading of 0.5 mol %. The product of the Suzuki reaction was isolated in a quantitative crude yield (9.54 g). The ratio of product to ketone 2 was 3:1. This yield was also concurrent with the smaller scale reactions.

The abiraterone acetate was purified by formation and crystallisation of its methanesulfonate salt from EtOAc/ MTBE. The salt was isolated in a 64% yield (7.65 g) and at 87.7% purity. This was subsequently recrystallised from a minimum volume of boiling isopropyl alcohol (95 cm$^3$) to yield the salt in 63% recovery (4.85 g) and at 96.4% purity.

Experimental

Triflate formation 3

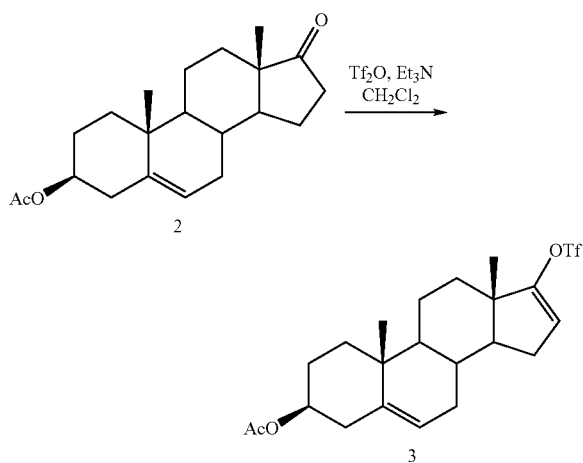

To a stirred solution of dehydroepiandrosterone acetate 2 (10 g, 30.3 mmol.) in CH$_2$Cl$_2$ (100 cm$^3$, 10 vol.) was added Tf$_2$O (5.60 cm$^3$, 33.3 mmol, 1.1 eq.) and the reaction was stirred at room temperature for five minutes. A solution of triethylamine (4.22 cm$^3$, 30.3 mmol, 1.0 eq.) in CH$_2$Cl$_2$ (100 cm$^3$, 10 vol.) was added over 25 minutes. The resulting purple solution was stirred at room temperature for 3.5 hours. The reaction was quenched by addition of water (150 cm$^3$, 15 vol.) and the layers separated. The aqueous layer was extracted with CH$_2$Cl$_2$ (75 cm$^3$, 7.5 vol.) and the organic layers were combined. The organic fraction was washed with 2N HCl (75 cm$^3$, 7.5 vol.) and brine (75 cm$^3$, 7.5 vol.). The organic layer was treated with MgSO$_4$ and activated charcoal (7.0 g, 0.7 wt eq.) for 10 minutes. The suspension was filtered through a pad of Celite™ and the filtrate was concentrated under reduced pressure to yield a brown oil, 11.20 g (80% crude yield). $^1$H NMR (CDCl$_3$) showed the ratio of product 3 to starting material 2 to be 3:1

Abiraterone acetate 1

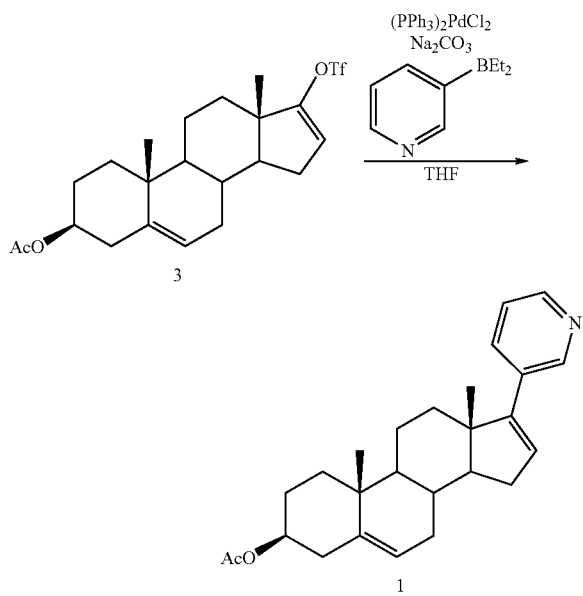

Pd(PPh$_3$)$_2$Cl$_2$ (97 mg, 0.14 mmol, 0.006 eq), diethyl (3-pyridyl)borane (6.11 g, 41.5 mmol, 1.7 eq.) and 2M Na$_2$CO$_3$ (aq) (55 cm$^3$, 111 mmol, 4.5 eq.) were added consecutively to a stirred solution of the mixture of triflate 3 and ketone 2 (11.20 g, 27.7 mmol assuming all substrate is triflate 3) in THF (130 cm$^3$, 10 vol.). The reaction was heated to 80° C. and stirred at this temperature for 5 hours. The reaction was cooled to room temperature and partitioned between ethyl acetate (130 cm$^3$, 11 vol.) and water (130 cm$^3$, 11 vol.). The layers were separated and the aqueous layer extracted with ethyl acetate (65 cm$^3$, 5.5 vol.). The combined organic layers were dried over MgSO$_4$ and concentrated under reduced pressure to yield a brown oil. This oil was stirred in MeOH (35 cm$^3$, 3 vol.) and was gently warmed with a hot air gun. A white solid (unreacted diethyl (3-pyridyl)borane) precipitated and was filtered. The filtrate was concentrated under reduced pressure to yield a brown oil (9.54 g, 100% yield). $^1$H NMR showed that this material was a 3:1 mixture of abiraterone acetate 1 and ketone 2.

Salt formation

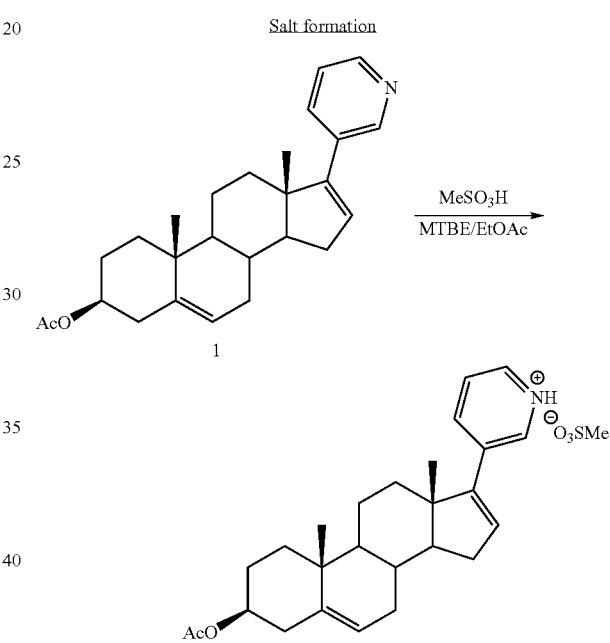

Methanesulfonic acid (1.86 cm$^3$, 25.6 mmol, 1.05 eq) was added to a stirred solution of the mixture of 1 and 2 (9.54 g, 24.4 mmol assuming entirely steroid 1) in a mixture of MTBE (50 cm$^3$, 5 vol.) and ethyl acetate (50 cm$^3$, 5 vol.). The resulting thick suspension was filtered and the cake washed with MTBE (10 cm$^3$, 1 vol.). The cake was dried in air to yield a tan solid (7.65 g, 64% yield based on all starting material being steroid 1, 87.7% purity by HPLC). The salt was recrystallised from boiling isopropyl alcohol (95 cm$^3$) to yield a tan solid (4.85 g, 41% yield, 96.4% purity by HPLC).

EXAMPLE 3

Further Investigations into Reaction Steps

As noted in Example 1, it has been noted that the formation of the triflate, 3, may depend on a number of factors:
 1. The nature of the base used in the reaction;
 2. The relative stoichiometries between the base and DHEA, 2;
 3. The nature of the solvent used;
 4. The reaction time.

Screen of Bases and Solvents for the Triflate Formation

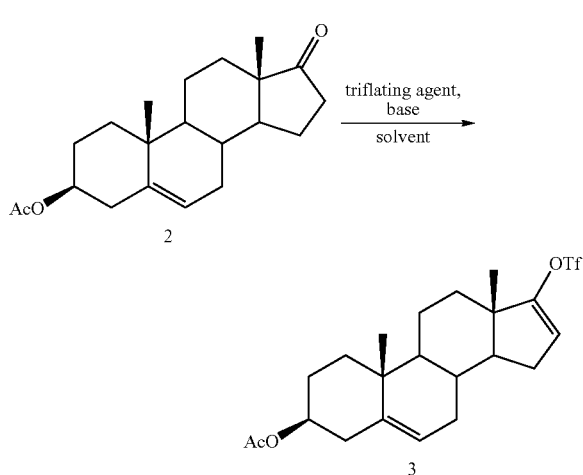

A range of bases of varying basicity and character was used in the formation of triflate, 3. Reactions using each of these bases were performed in a variety of solvents. Dichloromethane, 1,2-dichloroethane and chloroform were investigated in order to expand the range of chlorinated solvents utilised for the triflate formation. Ethyl acetate, methyl tert-butyl methyl ether and iso-hexane were studied in order to expand the nature of the solvents tested.

Each reaction was performed using 250 mg of DHEA, 2, in 20 volumes of the solvent. Trifluoromethanesulfonic anhydride (1.1 eq.) was added to the solution followed by the base (1.0 eq.) after 15 minutes. After 2 hours, a sample of each reaction was quenched into methanol and the reactions examined by LCMS.

Results are shown in Table 3.

the LCMS. The numbers quoted in the brackets were the conversion of DHEA, 2, to triflate, 3, not the overall yield of 3. A reaction which states a conversion to the triflate but decomposition also, would not give a good isolated yield under the conditions used. However the reaction may have given a better result if different conditions were attempted.

The table entries also show ("elim.") the amount of eliminated product, 5, present by NMR.

Bases whose conjugate acids have a relatively low $pK_a$ gave the worst results, with competing reactions causing complications. For instance the major product noted when N,N-diethylaniline was used was the de-acetylated product, 4. This was a significant product after extended reaction time when pyridine was used as the base.

Reactions performed in ethers and hydrocarbons showed problems with solubility of the reactant along with their reactivity.

Chlorinated compounds proved to be the optimal family of solvents for use in this reaction. It was noted that on the whole, reactions in dichloromethane and 1,2-dichloroethane were comparable whereas those in chloroform were retarded to some degree.

The levels of the eliminated product, 5, could not be detected by LCMS. Therefore selected samples were concentrated and the $^1$H NMR of the residue was taken. These samples were selected due to their higher levels of impurities

TABLE 3

Alternative bases for the formation of the triflate

|  | pKa of conjugate acid | CH$_2$Cl$_2$ | 1,2-dichloroethane | CHCl$_3$ | EtOAc | MTBE | $i$-hexane |
|---|---|---|---|---|---|---|---|
| Et$_3$N | 10.6 | ✓ (66) <5% elim. | ✓ (71) <5% elim. | ✓ (36) 9% elim. | ✓ (56) | X | ✓ (54) + decomp. |
| 2,6-lutidine | 6.75 | ✓ (70) 6% elim | ✓ (75) | ✓ (44) | ✓ (51) 10% elim. | X | X |
| pyridine | 5.21 | ✓ (80) + decomp 4% elim. | ✓ (78) + decomp | X | ✓ (52) + decomp 4% elim. | X | X |
| N,N-diethylaniline | 5.20 | X decomp | X decomp | X decomp | X decomp 6% elim. | X decomp | X decomp |
| DABCO | 8.82 | ✓ (29) 0% elim. | ✓ (44) | X | ✓ (57) + decomp 0% elim. | X | X |
| DBU | 12 | ✓ (54) 0% elim. | ✓ (70) | X | X | X | X |
| KO$^t$Bu | 17 | ✓ (61) | ✓ (63) | X | X | X | X |
| NaH | 36 | X | ✓ (73) + decomp | ✓ (67) | X | X | X |

✓ - triflate detected by HPLC (% conversion w.r.t. unreacted ketone).
X - no triflate detectable.

It should be noted that if a result notes that decomposition was occurring, a lot of unidentifiable peaks were present in shown in the LCMS. The level of the eliminated product was not detected at over 10% levels in any of the reactions and was not detected at all when DABCO and DBU were used.

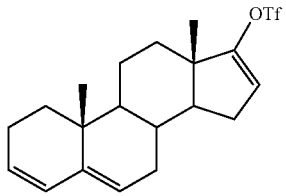

5

It should be noted that from the initial studies using 2,6-di-tert-butyl-4-methylpyridine that if the reaction was halted before completion, the levels of the eliminated product, 5, were much reduced. Only when the equivalents of the base were increased did the level of elimination increase. The bases subsequently used above never drove the reaction to completion. If excess base were used the reaction stalled and if the reaction time was extended other competing side reactions decomposed the product to species other than 5.

Optimisation of the Reaction Profile of the Triflate Formation.

It had already been noted that the addition rate of the base to the reaction had a major effect on the yield of the reaction. In addition, the product decomposed if the reaction was left unquenched overnight. The effect of the relative timings of the addition of $Tf_2O$ and $Et_3N$, as well as the total reaction time, were explored.

Each reaction was performed on a 500 mg scale under standard conditions. Samples were taken at the prescribed times and partitioned between ethyl acetate and water. The organic layer was concentrated and the residue tested by $^1H$ NMR.

Results are shown in Table 4. Any decomposition of the product was detected by the change in the shape of the aliphatic region of the spectra and could therefore only be qualitatively described.

TABLE 4 optimisation of the reaction profile of the triflate formation

| Time between $Tf_2O$ and $Et_3N$ addition (mins) | Time after $Tf_2O$ addition (mins) | % conversion | Decomposition? |
|---|---|---|---|
| 0.3 | 18 | 22 | None |
| | 65 | 27 | None |
| | 125 | 35 | None |
| | 245 | 39 | None |
| 15 | 18 | 50 | None |
| | 65 | 68 | Slight |
| | 125 | 75 | Some |
| | 245 | 75 | Significant |
| 60 | 18 | 21 | None |
| | 65 | 71 | Slight |
| | 125 | 75 | Significant |
| | 245 | 75 | Significant |

The first point to note is that the formation of the triflate started to occur without the presence of the base, but addition of the bases increased the rate of reaction.

The results also indicated that the reaction was essentially complete 1 hour after the addition of the base. Extension of the reaction time beyond an hour resulted in a reduction in the quality of the triflate due to decomposition of the product.

Any decomposition occurring was not forming the eliminated product, 5, but other unidentified compounds.

Examination of the Optimum Relative Stoichiometry for the Triflate Formation

It had already been noted that the use of large excesses of base lead to poor conversion of DHEA, 2, to the triflate, 3, and that use of large excesses of $Tf_2O$ lead to rapid decomposition of the product. We wanted to investigate the effect of changing the relative stoichiometry of the two reactants across a narrow range.

Each reaction was performed using 250 mg of DHEA under standard conditions. Triethylamine was added 15 minutes after the addition of $Tf_2O$ and the reaction sampled after 2 hours. Results are shown in Table 5.

TABLE 5 optimum relative stoichiometry for the triflate formation

| Eq. $Tf_2O$ | Eq. $Et_3N$ | Conversion after 2 hours[1] |
|---|---|---|
| 0.8 | 0.8 | 33% |
| 1.1 | 0.8 | 66% |
| 1.4 | 0.8 | 81% + decomposition[2] |
| 0.8 | 1.1 | 36% |
| 1.1 | 1.1 | 64%[2] |
| 1.4 | 1.1 | 83% |
| 0.8 | 1.4 | 40%[2] |
| 1.1 | 1.4 | 53% |
| 1.4 | 1.4 | 70% |

[1]Measured by LCMS
[2]Conversion confirmed by $^1H$ NMR.

These results confirmed that the number of equivalents of triflic anhydride needs to be higher than the number of equivalents of base for optimum conversion of DHEA to the triflate, 3. However, reducing the amount of base to sub-stoichiometric levels did not affect the conversion.

The invention claimed is:

1. A process for the preparation of a compound of the formula (III) by the triflation of a ketone of the formula (II)

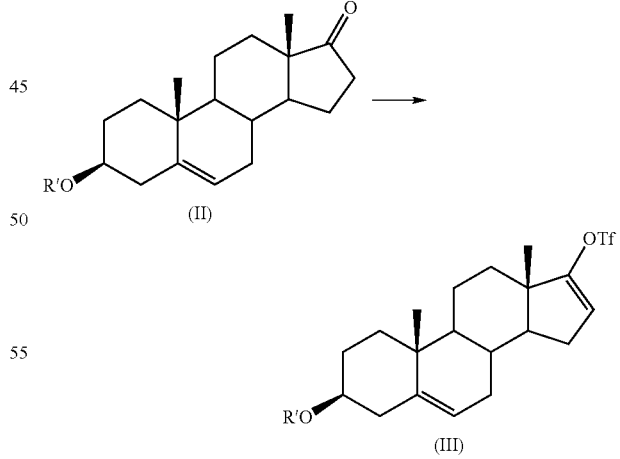

wherein R' represents hydrogen or a lower acyl group having 2 to 4 carbon atoms;
or a protected derivative thereof;
the triflating step being conducted in the presence of a base comprising a tertiary or heterocyclic amine such that the $pK_a$ of the conjugate acid at 25° C. is within the range 5.21 to 12, wherein the base is selected from the group consisting of pyridine, 2,6-lutidine, N-methylmorpholine, 1,4-diazabicyclo[2.2.2]octane (DABCO), trimethylamine, triethylamine, N,N-diisopropylethylamine (DIPEA), quinuclidine and 1,8-diazabicyclo[5.4.0]undec-7-ene (DBU).

2. A process as claimed in claim 1, wherein the base is 2,6-lutidine or triethylamine.

3. A process as claimed in claim 1, wherein the triflating step is carried out in a solvent comprising a chlorinated organic solvent or an organic ester.

4. A process as claimed in claim 1, wherein R' represents an acetyl group.

5. A process as claimed in claim 1, wherein the triflating step is effected using triflic anhydride ($Tf_2O$).

6. A process as claimed in claim 1, wherein the triflating step is effected using triflic anhydride ($Tf_2O$) and the base is added to the reaction mixture fifteen minutes or less after the triflic anhydride.

7. A process as claimed in claim 6, wherein the triflating step is performed using between 1.0 and 1.5 equivalents of triflic anhydride relative to the ketone of formula (II); and between 0.75 and 1.5 equivalents of base relative to the ketone of formula (II), wherein the number of equivalents of triflic anhydride is greater than or equal to the number of equivalents of base.

8. A process as claimed in claim 1, wherein the triflate of formula (III), or a protected derivative thereof, is reacted with a borane of formula $BZ^1Z^2Ar$, wherein Ar represents an optionally substituted five- or six membered fully unsaturated ring containing at least one nitrogen atom and $Z^1$ and $Z^2$ independently represent hydroxy or alkoxy or alkyl of 1-3 carbon atoms each or $Z^1$ and $Z^2$ together represent an alkylenedioxy group of 2 or 3 carbon atoms; in the presence of a palladium complex and a polar solvent to form a compound of the formula (I)

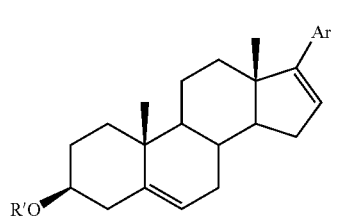

(I)

where Ar represents an optionally substituted five- or six membered fully unsaturated ring containing at least one nitrogen atom and joined to the main ring system by means of a carbon-carbon bond; and R' represents hydrogen or a lower acyl group having 2 to 4 carbon atoms;

or a pharmaceutically-acceptable salt thereof.

9. A process as claimed in claim 8 wherein Ar represents an optionally substituted five- or six membered fully unsaturated ring containing one or two heteroatoms, with at least one of them being nitrogen.

10. A process as claimed in claim 8, wherein Ar represents an unsubstituted five-membered fully unsaturated ring, or a six-membered aromatic ring optionally substituted with a single substituent.

11. A process as claimed in claim 8, wherein Ar represents a group:

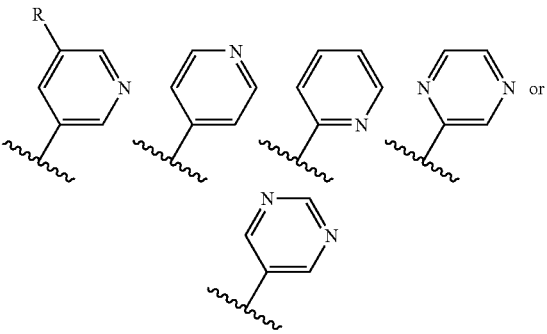

where R represents a hydrogen atom or an alkyl group of 1-4 carbon atoms.

12. A process as claimed in claim 8, wherein the compound of the formula $BZ^1Z^2Ar$ is a compound of the formula:

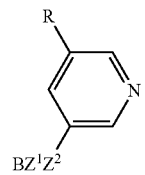

in which R represents a hydrogen atom or an alkyl group of 1 to 4 carbon atoms.

13. A process as claimed in claim 8, wherein the compound of formula I is a compound of formula:

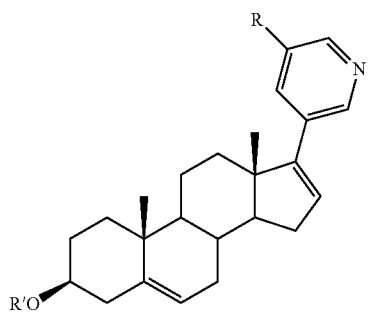

wherein R' represents hydrogen or a lower acyl group having 2 to 4 carbon atoms, and R represents a hydrogen atom or an alkyl group of 1-4 carbon atoms.

14. A process as claimed in claim 13 wherein R represents a hydrogen atom.

15. A process as claimed in claim 13 wherein R' represents an acetyl group.

* * * * *

UNITED STATES PATENT AND TRADEMARK OFFICE
CERTIFICATE OF CORRECTION

PATENT NO. : 8,236,946 B2  
APPLICATION NO. : 11/660792  
DATED : August 7, 2012  
INVENTOR(S) : Bury Page 1 of 1

It is certified that error appears in the above-identified patent and that said Letters Patent is hereby corrected as shown below:

In the Specification:

Column 5, line 48, please delete "lower acyloxy" and insert --lower acyl--.

Signed and Sealed this  
Twenty-sixth Day of November, 2013

Margaret A. Focarino  
*Commissioner for Patents of the United States Patent and Trademark Office*

UNITED STATES PATENT AND TRADEMARK OFFICE
CERTIFICATE OF CORRECTION

| | |
|---|---|
| PATENT NO. | : 8,236,946 B2 |
| APPLICATION NO. | : 11/660792 |
| DATED | : August 7, 2012 |
| INVENTOR(S) | : Bury |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1289 days.

Signed and Sealed this
Seventeenth Day of March, 2020

Andrei Iancu
*Director of the United States Patent and Trademark Office*